United States Patent
Platte et al.

(10) Patent No.: US 9,354,193 B2
(45) Date of Patent: May 31, 2016

(54) APPARATUS FOR MEASURING THE ELECTRICAL CONDUCTIVITY OF A LIQUID MEDIUM

(75) Inventors: Daniel Platte, Velbert (DE); Alfred Pohl, Essen (DE)

(73) Assignee: Optek-Danulat GmbH (DE)

( * ) Notice: Subject to any disclaimer, the term of this patent is extended or adjusted under 35 U.S.C. 154(b) by 348 days.

(21) Appl. No.: 14/117,942

(22) PCT Filed: Jun. 26, 2012

(86) PCT No.: PCT/EP2012/062278
§ 371 (c)(1),
(2), (4) Date: Nov. 15, 2013

(87) PCT Pub. No.: WO2013/010753
PCT Pub. Date: Jan. 24, 2013

(65) Prior Publication Data
US 2014/0152332 A1    Jun. 5, 2014

(30) Foreign Application Priority Data
Jul. 20, 2011 (DE) .......................... 10 2011 052 005

(51) Int. Cl.
G01R 27/08 (2006.01)
G01N 27/07 (2006.01)
G01N 27/06 (2006.01)

(52) U.S. Cl.
CPC ............... *G01N 27/07* (2013.01); *G01N 27/06* (2013.01)

(58) Field of Classification Search
CPC .................. G01N 27/06; G01N 27/07
USPC ............ 324/713, 722, 693, 694, 439
See application file for complete search history.

(56) References Cited

U.S. PATENT DOCUMENTS

| 2,173,233 A | * | 9/1939 | Lieneweg | ............ | G01N 27/045 324/443 |
| 3,757,205 A | * | 9/1973 | Dauphinee | ........... | G01N 27/045 324/118 |

(Continued)

FOREIGN PATENT DOCUMENTS

| DE | 42 16 176 | 11/1993 | ............. | G01N 27/06 |
| DE | 199 46 315 | 5/2001 | ............. | G01N 27/07 |

(Continued)

OTHER PUBLICATIONS

PCT/EP2012/062278 Written Opinion of International Search Authority, Aug. 30, 2012.*

(Continued)

*Primary Examiner* — Patrick Assouad
*Assistant Examiner* — Sean Curtis
(74) *Attorney, Agent, or Firm* — Kusner & Jaffe

(57) ABSTRACT

Device for measuring electrical conductivity of a liquid medium comprising constant voltage means, connected to a first electrode arrangement for injecting an alternating signal into the liquid medium, detection means, connected to a second electrode arrangement coupled via the liquid medium, for generating a measurement signal influenced by the electrical conductivity with a clock frequency (CLK) of the alternating signal, and evaluation means which from a current-proportional injection signal of the current injected by the first electrode arrangement into the liquid medium and from the measurement signal generate a conductivity signal of the liquid medium. The constant voltage means are made in an individual circuit branch which has commutator means for the first electrode arrangement and ohmic resistance means in a series connection, the current-proportional injection signal being tapped as a voltage drop over the resistance means.

32 Claims, 3 Drawing Sheets

(56) References Cited

U.S. PATENT DOCUMENTS

| | | | | |
|---|---|---|---|---|
| 3,820,392 A * | 6/1974 | Beck et al. | ............ | G01F 1/64 73/861.06 |
| 4,154,660 A * | 5/1979 | Micko | ............ | E21B 41/0021 204/412 |
| 4,266,188 A * | 5/1981 | Thompson | ............ | G01R 27/22 324/606 |
| 4,656,427 A * | 4/1987 | Dauphinee | ............ | G01N 27/07 204/400 |
| 4,691,169 A * | 9/1987 | Baum | ............ | G01N 33/1833 324/448 |
| 4,823,087 A * | 4/1989 | Sugimori | ............ | G01N 27/046 324/439 |
| 5,033,289 A * | 7/1991 | Cox | ............ | G01N 33/2823 324/689 |
| 5,260,663 A * | 11/1993 | Blades | ............ | G01R 27/22 204/402 |
| 5,272,444 A * | 12/1993 | Cox | ............ | G01N 27/221 324/664 |
| 5,341,102 A * | 8/1994 | Akiyama | ............ | G01R 27/22 324/202 |
| 5,488,300 A * | 1/1996 | Jamieson | ............ | G01R 31/3627 204/406 |
| 5,519,323 A * | 5/1996 | Kordas | ............ | G01R 27/22 257/532 |
| 5,543,717 A * | 8/1996 | Kordas | ............ | G01R 27/22 324/439 |
| 6,107,924 A * | 8/2000 | Kasai | ............ | G01V 3/102 324/204 |
| 6,259,242 B1 * | 7/2001 | Graham | ............ | G01N 15/1218 324/439 |
| 6,404,204 B1 * | 6/2002 | Farruggia | ............ | G01N 33/18 324/425 |
| 6,804,613 B2 * | 10/2004 | Ishikawa | ............ | G01F 1/60 141/94 |
| 7,135,870 B2 * | 11/2006 | Mohajer | ............ | G01N 22/00 324/639 |
| 7,629,800 B2 * | 12/2009 | Parachini | ............ | G01F 23/243 324/691 |
| 7,847,564 B2 * | 12/2010 | Rossi | ............ | G01R 27/22 324/439 |
| 8,076,950 B2 * | 12/2011 | Wee | ............ | G01N 33/1833 324/722 |
| 8,456,178 B2 * | 6/2013 | Wang | ............ | G01N 27/023 324/654 |
| 9,109,938 B2 * | 8/2015 | Molinaro | ............ | G01F 23/244 |
| 2003/0051557 A1 * | 3/2003 | Ishikawa | ............ | G01F 1/60 73/861.12 |
| 2004/0257094 A1 * | 12/2004 | Halalay | ............ | G01N 33/2888 324/698 |
| 2009/0267617 A1 * | 10/2009 | Seyfi | ............ | G01N 27/023 324/655 |
| 2011/0140717 A1 * | 6/2011 | Wang | ............ | G01N 27/023 324/654 |
| 2014/0152332 A1 * | 6/2014 | Platte | ............ | G01N 27/07 324/713 |

FOREIGN PATENT DOCUMENTS

| | | | | |
|---|---|---|---|---|
| DE | 10 2008 024 972 | | 12/2009 | ............ A61F 2/02 |
| WO | WO 2008/025775 | | 3/2008 | ............ G01R 27/06 |
| WO | WO 2008025775 A1 * | | 3/2008 | ............ G01N 27/06 |

OTHER PUBLICATIONS

Website printout of "JUMO tecLine Lf-4P Konduktive 4-Elektroden Leitfähigkeitsmesszellen," Jumo GmbH & Co. KG, Fulda, Germany, Sep. 29, 2009, Retrieved from the Internet: www.jumo.be/media/PDFs/Support_Download/product_archive/t20.2930de.pdf, print out date Aug. 20, 2012.

International Search Report for International Application No. PCT/EP2012/062278, Aug. 30, 2012.

* cited by examiner

APPARATUS FOR MEASURING THE ELECTRICAL CONDUCTIVITY OF A LIQUID MEDIUM

FIELD OF THE INVENTION

This invention relates to a device for measuring the electrical conductivity of a liquid medium, especially an aqueous medium according to the preamble of the main claim.

BACKGROUND OF THE INVENTION

These conductivity measurement devices have been known for a long time from the prior art in different circuit topologies and are used for the most varied applications. Here for example the industrial process engineering is important in which the conductivity of the fluids is checked in order to ascertain the concentration of dissolved salts in chromatography processes or the like. Typical specific conductivities in the range between roughly 50 mS/cm and 200 mS/cm can be detected here. In the field of control and monitoring of ultrafiltration processes conversely for example a range between 5 µS/cm and 100 µS/cm is especially relevant.

Another important application is the cleaning of process installations (for example the monitoring of flushing and cleaning processes), these installations being typically flushed with high-purity deionized water and the conductivity of this flushing water then being an indicator of reaching a desired cleaning state. The conductivities to be detected here are much smaller, typically less than 10 µmS/cm, certain requirements necessitating measurement errors or tolerances less than 0.5 µmS/cm. If for example, in this cleaning context, not only the flushing water, but also in addition for example a cleaning solution are to be monitored (typically somewhat heated NaOH, with conductivities of more than 100 mS/cm), in the conductivity measurement devices which are suitable for this purpose there is for example a need for systems which encompass a wide range of values of the conductivities of the relevant liquids to be detected.

The prior art furthermore discloses different measurement principles for measuring the conductivity in aqueous media. Thus for example to detect higher conductivity ranges inductive measurement methods are conventional, in which there is no (galvanic) contact of measurement electronics to the medium to be tested. But in particular in applications of the aforementioned type in which for example high-purity water is to be monitored in the microsiemens range, contact measurement methods are necessary, typically implemented by the feed and subsequent measurement of a measurement current via electrodes into the medium.

Due to the low conductivity of the medium, even at high electrode voltages the effective measurement currents are low, and moreover it can be assumed to be known that the current to be fed is provided as an alternating signal in order to keep low a voltage drop on the electrodes on the interface to the aqueous medium (relative to the actual voltage drop in the medium); electrolytic degrading influences on the electrodes are also avoided by this alternating signal.

It is considered known from the prior art to use in the so-called 2-pole measurement the same electrodes (as an electrode pair) both for the feed of the current and also for the measurement, and for example at low conductivities and accordingly optimized electrode geometry (typically then large-area electrodes with a small spacing are used) moderate injected voltages will yield easily measurable currents.

Then the specific conductivity (sigma) can be determined as:

$$\text{sigma} = G \times k = k \times I/U,$$

the cell constant k in the dimension length$^{-1}$ (typically 1/cm) indicating the special conditions of the respective measurement cell configuration, included electrode parameters and electrode geometries.

When the measurement range is expanded to higher conductivities, for example several 100 mS/cm, the voltage drop increases on the boundary layers of the electrodes, at the same time the voltage drop decreases over the aqueous medium which is to be measured. To solve these problems it can also be assumed to be known from the prior art to decouple the electrodes for a supplied current from the measurement electrodes for measuring the resulting voltage drop in the medium, in addition to increasing the measurement frequency (therefore for example a polarity reversal rate of the injected alternating signal). This leads to the fundamentally known approach of the 4-pole arrangement, by analogy to the generic 4-pole resistance measurement technology, a measurement current as an excitation current being fed via a first electrode pair into the aqueous medium (electrolyte) and then the measurement voltage (voltage drop) being detected via a second measurement electrode pair which interacts simply via the liquid medium. Both electrode pairs are thus three-dimensionally spaced apart from one another and separated. Since on the measurement and evaluation side there is typically a high internal resistance of the downstream detector electrodes, small currents flow accordingly in the output-side measurement circuit, with the advantageous action that the voltage drops on the interfaces of the measurement electrode pair are negligible. Since on the primary side (i.e. in the circuit which interconnects the injection electrodes) a current which flows there can be measured and managed, the primary-side electrode voltage drop is not important.

While, as described above, the 4-pole technology is favorably suited for measuring the electrical conductivity in aqueous media especially also for high conductivity values, it is nevertheless conventionally complex to implement this technology such that it encompasses a large conductivity range. In the practical implementation it has been found to be problematic that the cell constant (k) which is determined and calibrated for example generically using standardized environments is dependent on the actual conductivity. In addition the interfaces of the electrodes, which for example depending on the respective order of magnitude of the conductivity, cause current density shifts on the electrodes and in the electrolyte, as well as alternating current effects, play a part, such as for example parasitic capacitances (as loading of the secondary side voltage electrodes) or crosstalk, therefore an unintentional alternating current coupling between the primary side excitation circuit and secondary-side measurement circuit. Here for example in practice the (often long) feed lines between the electrode and measuring amplifier significantly influence these parasitic effects.

These problems are solved in the technologies which can be assumed from the prior art by evaluation-side measuring amplifiers which are specifically matched to different measurement and value ranges of the conductivities to be detected and are suitably switched over (manually or electronically); typical quantities to be influenced are respective frequencies, trigger currents and gains of a measuring amplifier. Integrated designs, for example microcontroller units, make available comfortable infrastructures which make a multistage adaptability to various conductivity ranges easily programmable.

One problem associated with this technological approach is in any case the necessary occurrence of discontinuities or jumps at transition sites of these measurement ranges; if therefore there is an aqueous fluid to be measured in this transition range, potentially unusable measurement results arise. Therefore the implementation of hysteresis during switchover is necessary, however such (also can be favorably implemented with digital electronics) a hysteresis approach entails the problem that a value which lies in the hysteresis range is dependent on the direction from which the measured value changes so that a hysteresis interval or deviation means a potential measurement error.

Just the aforementioned digital electronics in which for example digital processes electronics also generates a (rectangular) primary-side trigger signal for injection into the aqueous medium entails other problems of practical importance. Thus for example the harmonics of the base frequency which are associated with a rectangular pulse signal are especially greatly influenced by nonohmic interference, for example the aforementioned parasitic capacitances. This in turn can be opposed only by a sinusoidal (at least low-harmonic) primary-side triggering; this distinctly increases the hardware cost.

Finally, the possible variation of a measurement frequency during switchover of the range which can be assumed to be known (for example within the framework of an integrated-digital design) entails the potential problem of ambiguity by parasitic capacitive effects: If for example at very low conductivities a very high measurement frequency is used, these parasitic capacitive influences can feign high conductivity, with the unwanted effect that the secondary-side measuring amplifier does not recognize the appropriate measurement conditions and accordingly does not undertake a pertinent measurement range selection or switchover.

SUMMARY OF THE INVENTION

The object of this invention is therefore to devise a generic device for measuring the electrical conductivity of a liquid medium, especially an aqueous medium which is made and intended for detection of electrical conductivity in a large detection range, especially in the region between a few $\mu S/cm$ up to several 100 mS/cm, which is made structurally simple here, especially on the measurement side and evaluation side avoids a plurality of discrete measurement and evaluation ranges and/or discontinuous evaluation-side measurement signals, nevertheless offers a measurement signal of high signal quality and measurement accuracy which corresponds to the electrical conductivity.

The object is achieved by the device for measuring the electrical conductivity according to the main claim; advantageous developments of the invention are described in the dependent claims. In addition, protection within the framework of the invention is requested for a use of this device for measuring the conductivity of water and an aqueous solution, and this device will cover an uninterrupted conductivity range between 0.01 mS/cm and 500 mS/cm and beyond to more than 1 S/cm and will make it available as a hysteresis-free continuous measurement signal.

In a manner advantageous according to the invention, on the primary (injection) side an arrangement is formed from constant voltage means, commutator means for the first (injection) electrode arrangement and the ohmic resistance means as a series circuit in a (single) circuit branch, and the injection current can be tapped as a voltage drop over the resistance means (especially a partial resistance of it). Thus on the primary side the DC voltage which has been produced by the voltage source is applied via the commutator means as a modulator in clocked-changing polarity with the clock frequency to the injection electrode pair (as the preferred implementation of the first electrode arrangement). Depending on the conductivity of the aqueous medium (or the ohmic resistance means which are made preferably as constant resistance) an (injection) current flows which can be detected and evaluated as a voltage drop over the resistance means and is included in the determination of the electrical conductivity. Equally on the evaluation side demodulation occurs, in correct phase relation with the injection-side commutator means in the clock frequency by the detection means a storage capacitor being charged whose capacitor voltage can be tapped as the measurement signal, preferably quantified into a digital signal and likewise further processed electronically for determining the electrical conductivity.

The configuration as claimed in the invention, especially the circuit branch which is made on the injection side in a series connection advantageously enables the fact that over a wide range of the electrical conductivity of the aqueous medium the excitation current changes continuously depending on the conductivity, without as claimed in the invention other active components in this circuit branch being used (outside of the commutator means which are implemented in an otherwise known manner for example by means of semiconductor switches or the like, furthermore preferably without using an integrated circuit unit, or a programmable output of such a circuit unit). Accordingly the invention enables a change of conductivity of for example over five powers of ten to cause a change of the current flowing on the primary side in the circuit branch by roughly a factor of 30 (1.5 powers of ten), continuously and without discontinuities. Thus the wide range of the electrical conductivity which is to be measured in the aqueous medium, which range is intended as claimed in the invention, can then be advantageously encompassed without the necessity of choosing or switching over the range, and in addition advantageously only limited resolutions of assigned analog-digital (A/D) converters being necessary, with which then in addition the hardware cost can be reduced (and in addition the large series suitability of the invention is further increased accordingly). On the described dimensioning example then for the described range or its detection and evaluation by measurement engineering on the injection side and on the evaluation side one typical 16 bit converter with the pertinent resolution would be sufficient.

On the injection side, for example this analog-digital converter unit would convert the voltage signal which was tapped via the resistance means (or the partial resistance provided according to the development) and which is proportional to the injection current in the circuit branch and make it available for further digital processing, likewise as on the evaluation side one analog-digital converter unit for digitizing the capacitor voltage is assigned to the capacitance means which interact with the second electrode arrangement (i.e. the measurement electrodes).

The invention is especially relevant and advantageous for practical implementation when the advantages of simplification offered by the above described invention principle are implemented using simple and economical electronic modules. In addition to the described, potentially economical A/D converters which are available as mass-produced parts, for this purpose especially the implementation of the evaluation means by means of suitable microcontrollers is recommended, for example the injection and measurement signal which has been digitized according to the development separately from such a controller unit likewise reducing the (hardware) requirements for such an electronic component, such as for example the serial coupling of the A/D converter units provided on the injection side and/or measurement side, which coupling is provided according to the development; in this way advantageously the number of controller terminals can be distinctly reduced, equally the primary side and secondary side can be interrogated in a timely manner or synchronously and then further processed in terms of data.

In particular, the implementation of the commutator means which is advantageous according to the development using electronic switching components, for example suitable (power) transistors, leads to potentially disruptive higher frequency signal components in the primary side circuit branch, optionally also on the measurement side. In addition a trigger signal for the commutator means (in the clock frequency) influences this signal picture. Accordingly it is provided according to the development that suitable filter means be provided in the primary-side circuit branch and/or on the evaluation side/measurement side, for example in the form of a capacitor in parallel to the measurement resistor. It is also advantageous and preferred according to the development to use the (digital) filter means which are often integrated into the analog-digital converter units to filter (matched for example to the clock frequency of the alternating signal) a noise influence in this respect out of the measurement circuits (this applying equally for example to the influences of a line frequency of an existing supply voltage or to other superimposed noise alternating signals).

Another preferred embodiment of the invention calls for (noncapacitive) decoupling means, especially ohmic resistances, to be provided between the electrodes of the second electrode arrangement and the downstream measurement-side commutation. This development measure, in contrast to traditional logic to connect the measurement-side voltage electrodes with low resistance to the measurement capacitor and the downstream quantization or evaluation electronics, causes an influence of the voltage electrodes (for example thickness and homogeneity of a passive layer) in concert with charge effects and potential effects in commutator edge change to have much less an effect on the secondary side measurement signal.

This measure would alternatively also be possible for example by an especially high-resistance configuration of the commutator input; this design which is advantageous and simple in terms of hardware according to the development using discrete semiconductor components would require however additional cost here.

While within the scope of implementations as claimed in the invention it is advantageous and useful on the secondary side (i.e. on the side of the second electrode arrangement and the assigned detection means) to amplify and then suitably digitize the voltage signal arising via the capacitor means with a constant gain (or to digitize it unamplified), one version of the invention which is advantageous according to the invention calls for the capacitor voltage to be amplified in the form of amplifier units provided parallel to one another by different gains and accordingly to offer the amplified capacitor voltage signal (simultaneously) at different levels; this high resistance of operational amplifiers which are typically used for this purpose likewise little opposes this parallel arrangement of two or more amplifier units, such as for example according to another version, on the one hand the capacitor voltage signal is directly digitized and then made available likewise continuously for further processing, as a capacitor voltage signal which has been amplified by a predetermined gain before digitization in a separate, firmly assigned A/D converter.

In the further processing by the evaluation means then this version of a simultaneous multiple measurement signal at different voltage (amplification) levels enables the maximum possible flexibility in the evaluation and the further processing of the signal which has been acquired: Thus for example at high capacitor voltage levels an unamplified signal can be digitized and further processed (for example an amplifier which potentially overdrives at such a high voltage level remaining by controlled decrease in a high-resistance range which thus does not influence the measurement voltage), while for example a low-level capacitor voltage which unamplified would yield only a very noisy A/D conversion result can first be raised by the predetermined and known gain. In one possible transition range in turn the signal of the two measurement branches (since present continuously and in parallel) can be combined or computed with suitable weightings.

In turn the circumstance is advantageous and of practical importance that the A/D converter units which are assigned on the primary side and secondary side, according to the development separated from a microcontroller control unit, acquire the same operating or reference voltage of a supply voltage unit which is present for the entire device. This advantageously leads to the fact that corresponding errors due to fluctuations or other effects of the reference voltage are equalized and leave the measurement result unaffected. This also applies equally to the necessary quantization of a temperature signal by means of an A/D converter which conditions the analog temperature signal of a temperature sensor which is assigned to the aqueous medium according to another advantageous development of the invention.

As a result, this invention surprisingly makes it possible easily, effectively and powerfully for a large continuous range of electrical conductivity of a liquid medium to be covered, typically between 1 µmS/cm and 1000 mS/cm without the necessity of complex and fault-susceptible switching over of the range, without increased measurement engineering and evaluation engineering cost on the secondary side, and without the electrolytic and other effects associated with the electrode pairs significantly influencing a measurement result. Here the O-pole technology in which both the first and also the second electrode arrangement each have one electrode pair is preferred, nevertheless constellations are conceivable in which more than two electrode pairs, on the injection side and/or measurement side, are provided in the measurement cell and are wired in the device as claimed in the invention.

According to the design, cable influences or other capacitively active factors are advantageously minor so that they have no adverse effects, in an essentially useful manner. Likewise an electrical (total) power demand of the device is low, favorable especially in a power supply which is isolated according to the development and which facilitates a low-capacitance design. In isolation according to the development, a coupling capacitance parallel to the isolation barrier of less than 5 pF can be implemented; this in turn reduces the occurrence of noise potentials.

BRIEF DESCRIPTION OF THE DRAWINGS

Other advantages, features and details of the invention will become apparent from the following description of exemplary embodiments as using the drawings.

DETAILED DESCRIPTION OF THE INVENTION

Figure 1:
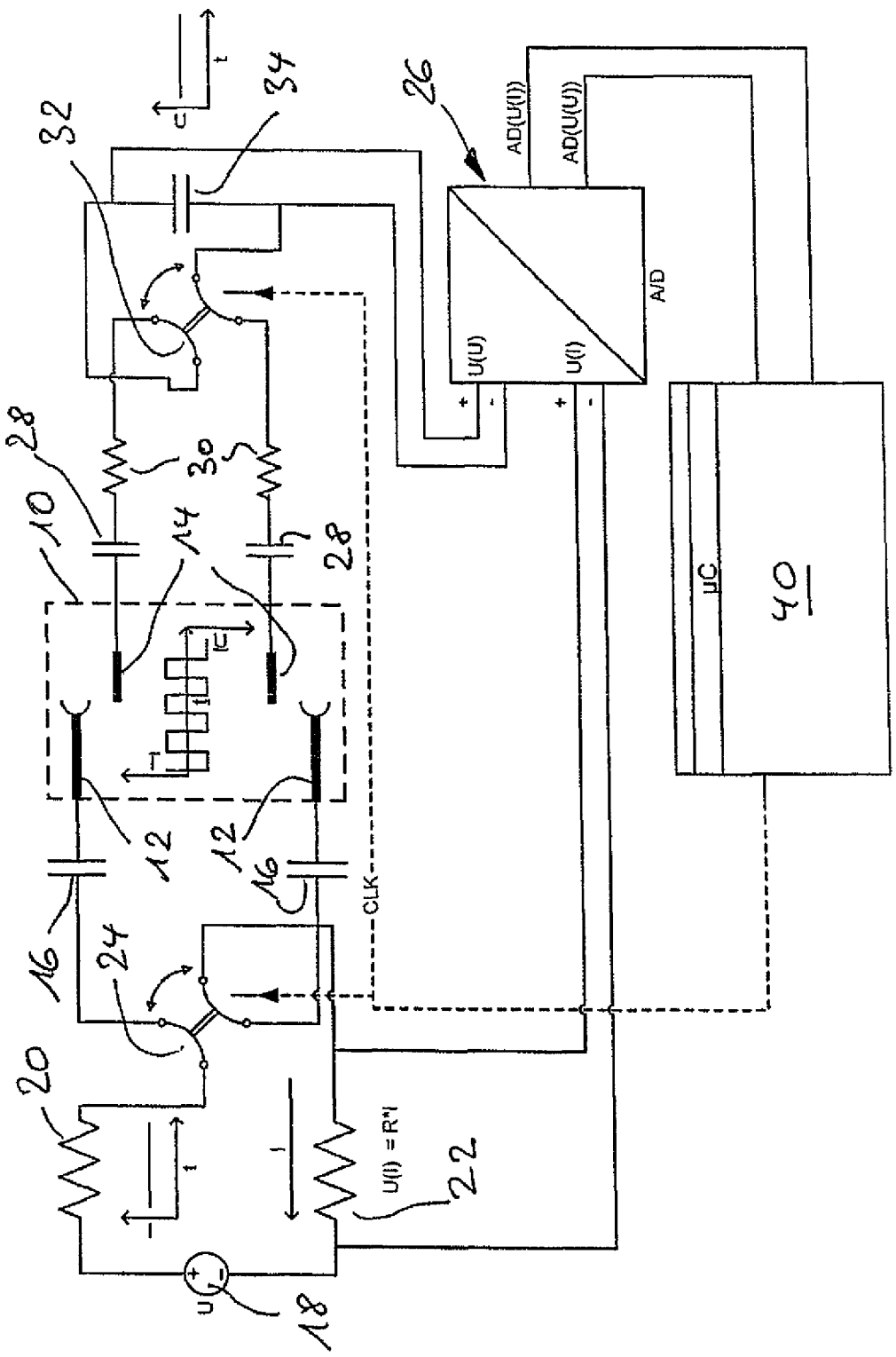
FIG. 1 shows a schematic block diagram for illustration of the fundamental operating structure of this invention.

FIG. 1 illustrates in the schematic the important functional components of the device for measuring the electrical conductivity of an aqueous medium according to a first embodiment of this invention. Thus reference number 10 describes a measurement cell which can be filled with the liquid medium, and into which one electrode pair 12 projects as a first electrode arrangement and another electrode pair 14 projects as a second electrode arrangement, decoupled from one another, in order to undertake injection in the manner of an otherwise known 4-pole arrangement via the electrodes 12 and then to generate the measurement signal by means of the electrodes 14. For purposes of more extensive disclosure, especially with respect to one possible practical implementation on the exemplary embodiment, reference is made to the measurement cell which is disclosed in DE 199 46 315 and which shows one possible example for implementation of the cell 10 which is shown in FIG. 1.

On the injection side, i.e. as a circuit branch connected to the electrode pair 12 (and via the DC potential coupled to the coupling capacitors 16 which decouple the electrodes), there is a constant voltage source 18 which is connected via a first resistor 20 (as a working resistor) and a second resistor 22 (measuring resistor) to the primary-side commutator means 24 which in turn, triggered by a clock signal CLK, make an alternating signal for the electrode pair 12 with the clock frequency CLK in the described manner from the constant voltage signal of the source 18. In each commutator switching state there is an individual circuit branch on the injection side, the voltage source 18 forming a series connection to the resistance means which have been formed from the resistors 20, 22 and to the electrode pair 12. A current which flows in this circuit branch drops over the resistor 22 and is tapped there as an injection-side, current-proportional injection signal (U)I and supplied to an A/D converter unit 26.

On the measurement side is the potential of the electrode pair 14 (coupled or decoupled by respective coupling capacitors 28 or coupling resistors 30 which are in series) over a secondary-side commutator unit 32 via a measurement capacitor 34, the capacitor voltage U(U) being tapped as the measurement signal and present at the A/D converter unit 26.

Since the secondary-side commutator unit 32, clocked with the clock frequency CLK and operated synchronously to the primary-side unit 24, demodulates the signal which has been modulated rectangularly for the injection in the illustrated manner on the output side there is a capacitor DC voltage over the measurement capacitor 34 as the measurement voltage U(U).

In the further processing as evaluation means both the current-proportional injection signal U(I) and also the measurement signal U(U) are then present in quantized digital form which is to be transmitted serially as AD (U(U)) and AD (U(I)) and are processed in an assigned microcontroller unit 40. This microcontroller unit at the same time generates in an otherwise known manner the alternating clock CLK for the primary-side and secondary-side commutators 24, 32 which, not shown in the figures and in an otherwise known manner, are implemented by means of discrete semiconductor switches (or as commutator transistors which have been integrated into a semiconductor module, optionally with additional integrated means for compensation of the charge injection and with delay elements for the clock signal in order to avoid transient short circuits when the edge changes). From the ratio of the current injected on the primary side and voltage measured on the secondary side (with consideration of the cell constant and in addition of necessary calibration constants, including an offset for current, voltage and conductivity) the microcontroller unit then either itself computes the value of the electrical conductivity or alternatively prepares the individual quantized variables for external further processing via a suitably chosen protocols.

Figure 2:
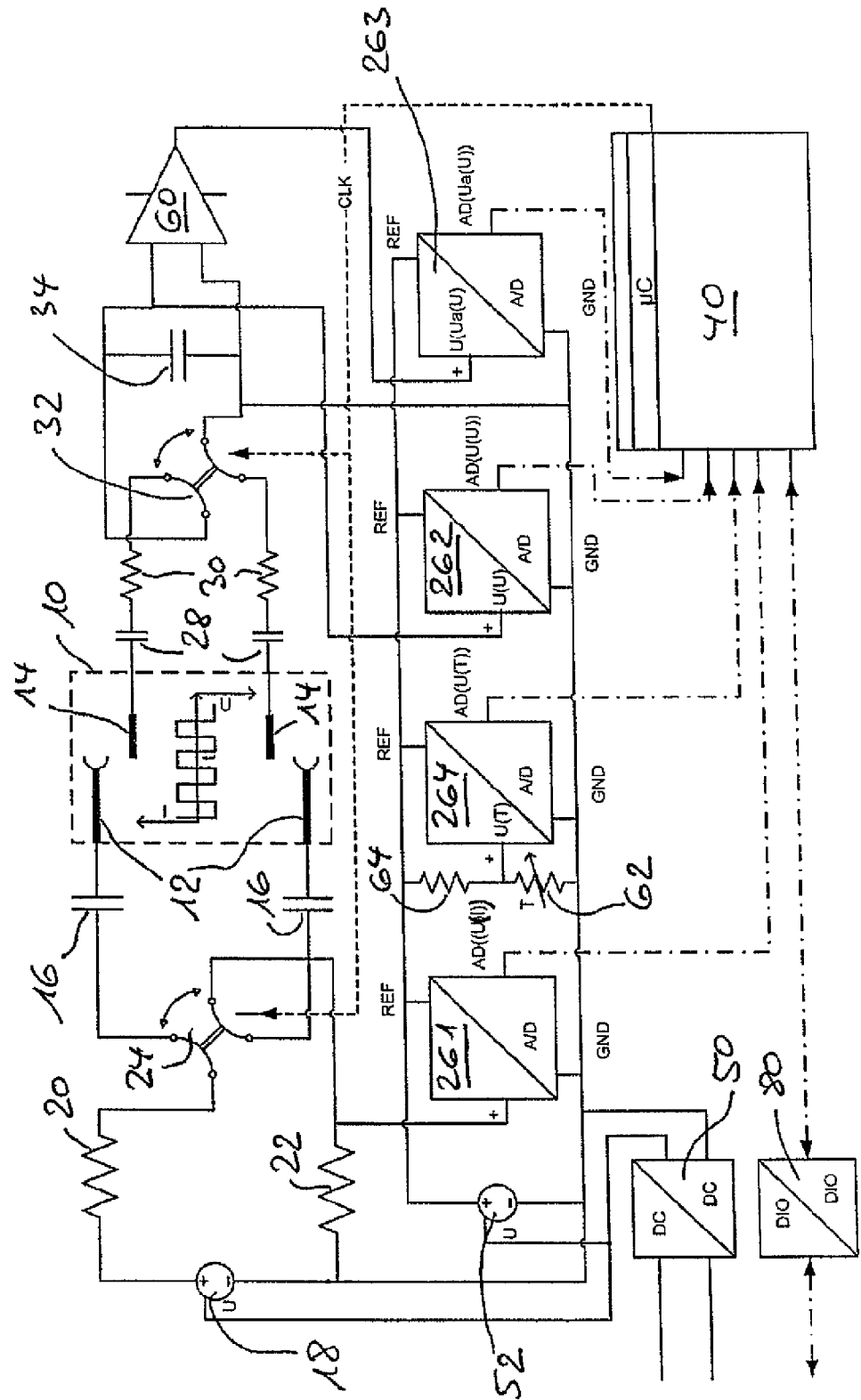
FIG. 2 shows a representation analogous to FIG. 1, but with additional circuit components and modules which are advantageous for practical implementation.

The schematic circuit diagram of FIG. 2 which is made analogously to FIG. 1 illustrates additional components of the described exemplary embodiment which are useful in the practical implementation, the same reference numbers describing identical functional components or functionalities. This arrangement, with the exception of the measuring cell 10 and temperature sensors which are assigned to it (symbolized with reference numbers 62, 64), with correspondingly short cable connecting lengths and small parasitic capacitances, is integrated into a body of cuboidal shape 18 mm×47 mm×10 mm, therefore implements an advantageously small compact size. The block circuit diagram of FIG. 2 shows details of the A/D converter arrangement which is only schematically suggested in FIG. 1 as a plurality of converters; a first 16 bit converter unit 261 with an integrated digital filter unit (not shown in detail) which is tuned to a line frequency of a supply voltage unit 50 (more accurately: a DC-DC converter unit with electrical isolation; in one practical implementation supplied by a higher-level feed unit with 5V DC voltage, then for example an unregulated supply voltage of roughly 10V DC being present on the voltage source 18) receives the injection current-proportional voltage signal U(I) which drops over the resistor 22 and converts this 16 bit signal AD ((U)I) which has been quantified with a reference voltage REF of 2.7 V for the microcontroller unit 40. The reference voltage REF is generated from a reference voltage unit 52 which is in turn supplied from the unit 50 (like otherwise also the constant voltage unit 18).

Equally a second A/D converter unit 262 (which receives the same supply and reference voltage REF as the unit 261) generates from the measurement voltage signal (U)U which is dropping over the measurement capacitor 34 the 16 bit-quantified and serial measurement signal AD (U(U)), in turned prepared on the microcontroller unit 40.

As a variation and an addition to the generic implementation of FIG. 1, the exemplary embodiment of FIG. 2 additionally shows how the measurement voltage signal U(U) as a capacitor voltage is present additionally at the input of a measurement amplifier unit 60, in the exemplary embodiment a gain 21 is preset (relative to the unamplified capacitor voltage U(U). This amplified signal Ua(U) is processed, analogously to the quantization of the unamplified measurement signal and of the injection current signal, by a third A/D converter unit 263, in turn resolution 16 bit and serial output as AD (Ua(U)) to the microcontroller unit 40, with the action that according to FIG. 2 the measurement voltage is present twice in parallel over the capacitance 34, specifically on the one hand as an unamplified signal, on the other hand as raised in level by the amplifier unit 60 for processing by the microcontroller unit 40.

In turn, in addition to the generic principle of FIG. 1, FIG. 2 shows still a fourth 16 bit A/D converter 264 which converts a temperature signal which has been tapped from a temperature sensor T into a corresponding serially digitized temperature signal AD (U(T)). This analog temperature signal U(T) which solely for reasons of schematic simplification is shown as a temperature-proportional voltage signal which drops over a temperature-variable resistor 62 relative to a reference resistor 64, illustrates a temperature detection of the aqueous medium which is contained in the measuring cell 10, either the temperature sensor 62, suitably transferring heat, being attached to the measuring cell or projecting into it for detection of a current fluid temperature. The representation furthermore illustrates that the illustrated temperature measurement (as also the conductivity measurement) is independent of a supply or reference voltage of the A/D converter units 26*i* which is supplied in parallel: In the illustrated temperature measurement specifically the digitized value depends also only on the ratio of the resistances 62, 64, but not on the reference voltage REF since the voltage divider 62/64 and the AD/converter 264 are between the same voltage.

The microcontroller unit 40 then prepares the digitized signals of the converters 261 to 264 which have been obtained in this way for output via an interface module 80 for optical decoupling of the digital signals (clock, digital in/out=DIO, in addition to the DC/DC converter unit 50 this module 80 constituting a main source of parasitic coupling via the potential barriers, in total roughly 5 pF), either the microcontroller unit 40 having undertaken signal processing, or however only according to a desired transmission protocol, then the acquired signals being available for further treatment by the unit 80.

Possible galvanic decoupling of the supply unit 50 from the primary-side and secondary-side measurement circuits and from the pertinent A/D conversion is not shown in FIG. 2.

In the specific implementation, structure of the measuring cell for example according to DE 199 46 315, cell constant 0.35/cm, the illustrated device would be at a clock frequency of commutator changing of 10 kHz (this clock frequency in the range between roughly 1 and roughly 100 kHz has proven favorable on the one hand to be fast enough to reduce the disadvantageous voltage drop on the electrodes, on the other hand of sufficiently low frequency for reducing disadvantageous switching effects) is then combined with a typical repetition or interrogated rate of the A/D conversion by the units 261-264 of 0.1 seconds (a typical conversion time of roughly 80 ms, after this time a respective measured value is available; with a clock rate of 30 kHz the digital signal is clocked out from the converter via the serial interface), for a roughly synchronous acquisition of the data. Since moreover, as explained as advantageous within the framework of the invention, all converters 261-264 are operated with the same supply and reference voltage, noise influences do not affect the measurement result. A typical total power consumption of the circuit is in the range of <250 mW so that, as discussed, low coupling capacitances are sufficient for galvanic decoupling, A conductivity sigma of the fluid contained in the tank 10 would now be determined as follows:

$$\text{sigma} = \left( \frac{AD(U(I)) - ADio}{AD(U(U)) - ADuo} \cdot \frac{1}{R_{mess}} \right) - \text{sigma}_o \quad (1.1)$$

$$\text{sigma} = \left( \frac{AD(U(I)) - ADio}{AD(U(U)) - ADuo} \cdot \frac{21}{R_{mess}} \right) - \text{sigma}_o \quad (1.2)$$

and according to formula 1.1 and no amplification of the capacitor signal a large measurement range can be covered, while, especially in the region of small conductivities, then as the amplified signal (factor 21) according to formula 1.2, the data stream AD (Ua(U)) is available.

In the formulas $AD_{IO}$ (as the offset for the current measurement), $AD_{UO}$ (as the offset for the output-side voltage measurement), $sigma_0$ (as the offset for the conductivity, for example for taking into account cable and installation effects) mean calibration constants which are set or selected suitably and in the already described manner k means the cell constant and therefore takes into account the geometry of the measuring cell. Since within the framework of the invention the cell constant k is well defined via the measuring cell geometry, it can be reproducible defined via suitable process control (as mechanical accuracy). To determine the constant $AD_{UO}$ and $sigma_0$ an open state (i.e. air, therefore unfilled measuring cell) is induced, while for example the offset $D_{IO}$ can be determined by a short circuiting of the electrodes. Accordingly the (traditionally problematic) handling of liquid conductivity standard media for calibration is eliminated. Since moreover $sigma_0$ describes essentially an apparent conductivity by capacitances which are parasitic in parallel to the electrodes 14 (see in this respect also the voltage decrease in the range between 0 µS/cm and 20 µS/cm in FIG. 3), this conductivity in practical use is reduced to roughly $sigma_0 = 2.5$ µS/cm.

Figure 3:
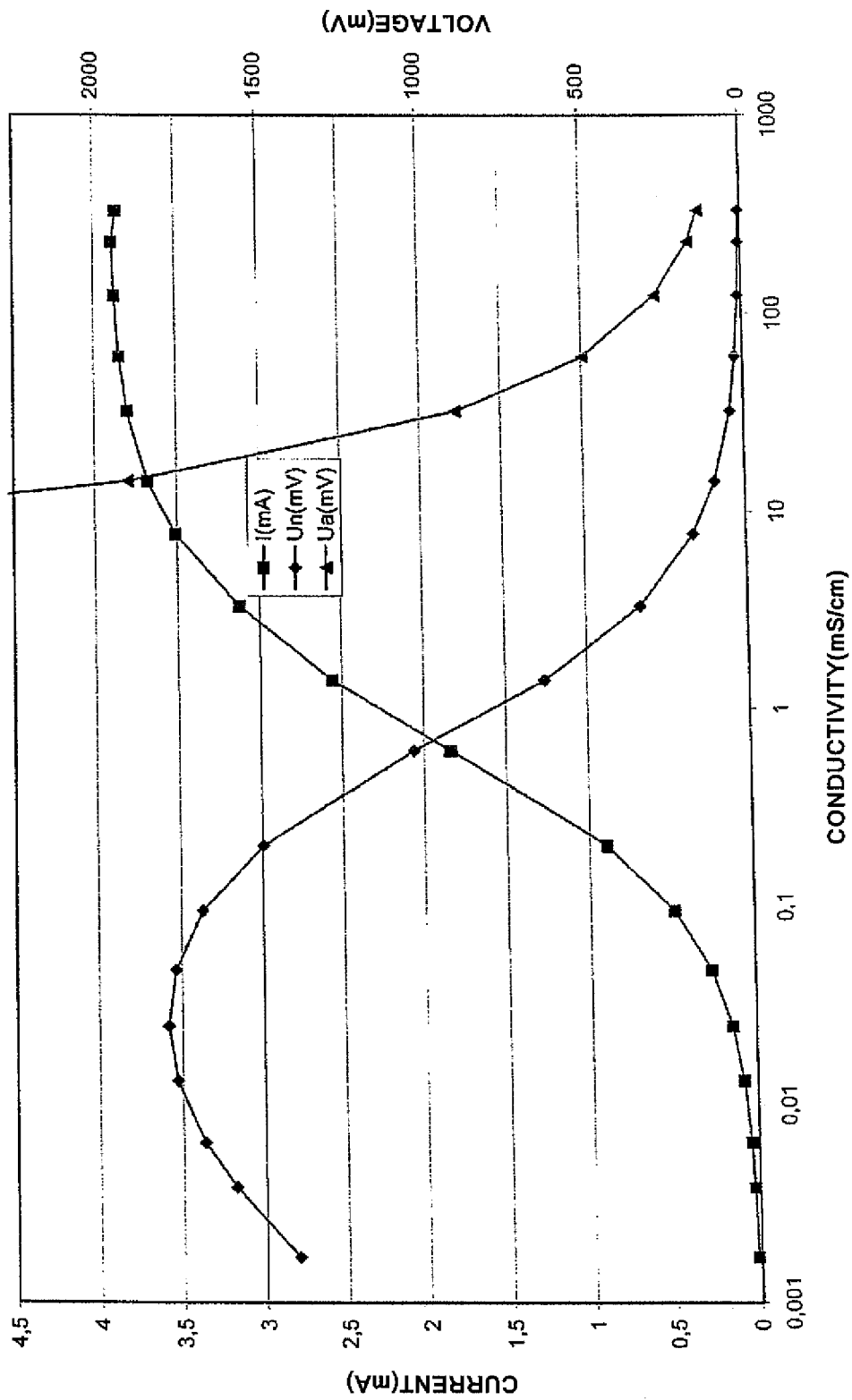
FIG. 3 shows a current and voltage diagram, relative to the electrical conductivity, for illustration of a conductivity dependency over a large detection range.

A specific signal behavior of this circuit, especially a characteristic of the (injection-side) current as well as, associated therewith, characteristics of the measurement-side measurement voltages (amplified as Ua and unamplified as Un) illustrate the signal characteristics of FIG. 3. It is shown that over a very wide range of conductivities, from roughly 2 µS/cm to roughly 200 mS/cm, the injection-side current varies between roughly 0.01 and roughly 3.8 mA, while there are voltages which are unamplified on the measurement side between roughly 10 mV and roughly 1700 mV; just the region of high conductivities makes the use of the amplified voltage signal beneficial since here, at correspondingly low injection-side current flows, an unamplified voltage measurement signal no longer yields sufficient resolution. In fact, up to roughly 200 mS/cm the resolution remains better than 0.6% of the measured value so that up to this value the amplified branch can be fundamentally omitted.

In the practical implementation this behavior means that both in the left-side region of FIG. 3, at small specific conductivities, and also in the right-side region of large conductivities, good resolutions can be achieved, only on the boundaries of the measurement range, i.e. at 2 µS/cm or 200 mS/cm (relative to the unamplified branch) the resolution reaching the described region of 0.6%, but in between for many measurement tasks it is already completely sufficient and thus generally does not require the additional amplified branch which is shown in the exemplary embodiment.

Having described the invention, the following is claimed:

1. A device for measuring an electrical conductivity of a liquid medium, comprising:
   constant voltage means for injecting an alternating signal into the liquid medium, the constant voltage means electrically connected to a first electrode arrangement,
   detection means for generating a measurement signal influenced by the electrical conductivity of the liquid medium, the measurement signal having a clock frequency of the alternating signal, wherein the detection means is electrically connected to a second electrode arrangement, which is physically separated from the first electrode arrangement and which is electrically coupled to the first electrode arrangement via the liquid medium, and
   evaluation means for generating an output signal from (i) a current-proportional injection signal of current injected by the first electrode arrangement into the liquid medium and (ii) the measurement signal, said output signal provided for further electronic processing, wherein the constant voltage means is located in a circuit branch having a first commutator for the first electrode arrangement and ohmic resistance means for providing a source of ohmic resistance, the first commutator and the ohmic resistance means connected in series with the constant voltage means, and wherein the current-proportional injection signal is tapped as a voltage drop over a resistor of the ohmic resistance means.

2. The device as claimed in claim 1, wherein the device further comprises:

a first analog-digital converter unit for generating a digital current-proportional injection signal, wherein the first analog-digital converter unit is not integrated into the evaluation means and is assigned to the ohmic resistance means.

3. The device as claimed in claim 2, wherein the device further comprises:

a second analog-digital converter unit for generating a digital measurement signal, wherein the second analog-digital converter unit is not integrated into the evaluation means and is assigned to capacitance means which interacts with the second electrode arrangement.

4. The device as claimed in claim 2, wherein the first analog-digital converter unit generates a serial output signal that is transmitted to the evaluation means via a serial connecting line assigned to the first analog-digital converter unit.

5. The device as claimed in claim 2, wherein the first analog-digital converter unit has integrated filter means tuned to the clock frequency of the alternating signal and/or of a supply voltage signal.

6. The device as claimed in claim 2, wherein the device further comprises:

a common voltage supply unit assigned to the first analog-digital converter unit, wherein the common voltage supply unit serves as a supply voltage unit for the constant voltage means and/or the common voltage supply unit is integrated into the first analog-digital converter unit and/or the first analog-digital converter unit has a common reference voltage source for converter quantization.

7. The device as claimed in claim 1, wherein the constant voltage means includes an analog control unit and/or the constant voltage means is implemented without integrated digital circuit modules.

8. The device as claimed in claim 1, wherein the device further comprises:

temperature detection means for detecting a temperature of the liquid medium, the temperature detection means interacting with the evaluation means via a third analog-digital converter unit, wherein the temperature of the liquid medium influences the conductivity signal.

9. The device as claimed in claim 1, wherein the circuit branch is configured such that the ohmic resistance means is invariable, free of hysteresis and not able to be discretely switched over or selected, and/or there are no active and/or switching elements in the circuit branch which influence an ohmic resistance value of the ohmic resistance means.

10. The device as claimed in claim 3, wherein the detection means includes a capacitor having a capacitor voltage that determines the digital measurement signal which is generated continuously and/or independently of the clock frequency of the alternating signal.

11. The device as claimed in claim 1, wherein the measurement signal is present parallel and synchronously on a first and a second input of the detection means with signal levels which have been amplified to different degrees from one another.

12. The device as claimed in claim 2, wherein a repetition frequency and/or a cycle frequency of the generation of the digital current-proportional injection signal is set up to the clock frequency of the alternating signal in a ratio of less than 1:100.

13. The device as claimed in claim 1, wherein the device further comprises:

decoupling means located between respective electrodes of the second electrode arrangement and a second commutator downstream of the respective electrodes of the second electrode arrangement.

14. A method for measuring an electrical conductivity of a liquid medium, comprising:

injecting an alternating signal into the liquid medium, wherein the alternating signal is injected by constant voltage means electrically connected to a first electrode arrangement, generating a measurement signal influenced by the electrical conductivity of the liquid medium, wherein the measurement signal has a clock frequency of the alternating signal, the measurement signal generated by a detection means electrically connected to a second electrode arrangement, said detection means physically separated from the first electrode arrangement and electrically coupled to the first electrode arrangement via the liquid medium, and generating a conductivity signal of the liquid medium, wherein the conductivity signal is generated by evaluation means from (i) a current-proportional injection signal of current infected by the first electrode arrangement into the liquid medium and (ii) the measurement signal, and providing the conductivity signal for further electronic processing, wherein the constant voltage means is located in a circuit branch having a commutator for the first electrode arrangement and ohmic resistance means in a series connection, wherein the current-proportional injection signal is tapped as a voltage drop over the ohmic resistance means, and wherein the conductivity signal of the liquid medium has an uninterrupted range of conductivity between 0.001 mS/em and 1000 mS/cm.

15. A device as claimed in claim 1, wherein the liquid medium is an aqueous medium.

16. A device as claimed in claim 1, wherein the second electrode arrangement is an electrode pair.

17. A device as claimed in claim 1, wherein the detection means is coupled via the liquid medium in the manner of a four-pole configuration.

18. A device as claimed in claim 1, wherein the output signal is a conductivity signal of the liquid medium.

19. A device as claimed in claim 1, wherein the current-proportional injection signal is tapped as a voltage drop over a partial resistor of the ohmic resistance means.

20. The device as claimed in claim 3, wherein the second analog-digital converter unit generates a serial output signal for the evaluation means and interacts with the evaluation means via a serial connecting line, which is assigned individually to the second analog-digital converter unit.

21. The device as claimed in claim 3, wherein the second analog-digital converter unit has integrated filter means tuned to the clock frequency of the alternating signal and/or of a supply voltage signal.

22. The device as claimed in claim 3, wherein the device further comprises:
a common voltage supply unit assigned to the second analog-digital converter unit, wherein the common voltage supply unit serves as a supply voltage unit for the constant voltage means and/or the common voltage supply unit is integrated into the second analog-digital converter unit and/or the second analog-digital converter unit has a common reference voltage source for converter quantization.

23. The device as claimed in claim 1, wherein the device further comprises:
a second analog-digital converter unit for generating a digital measurement signals, wherein the second analog-digital converter unit is not integrated into the evaluation means and is assigned to capacitance means which interacts with the second electrode arrangement.

24. The device as claimed in claim 23, wherein the second analog-digital converter unit generates a serial output signal that is transmitted to the evaluation means via a serial connecting line assigned individually to each of the first and second analog-digital converter units.

25. The device as claimed in claim 23, wherein the second analog-digital converter unit has integrated filter means tuned to the clock frequency of the alternating signal and/or of a supply voltage signal.

26. The device as claimed in claim 23, wherein the device further comprises:
a common voltage supply unit assigned to the second analog-digital converter unit, wherein the common voltage supply unit serves as a supply voltage unit for the constant voltage means and/or the common voltage supply unit is integrated into the second analog-digital converter unit and/or the second analog-digital converter unit has a common reference voltage source for converter quantization.

27. The device as claimed in claim 9, wherein the ohmic resistance means has a constant ohmic resistance value.

28. The device as claimed in claim 12, wherein the ratio is less than 1:500.

29. The device as claimed in claim 13, wherein the decoupling means is ohmic resistance means.

30. The method as claimed in claim 14, wherein the liquid medium is water.

31. The method as claimed in claim 14, wherein the uninterrupted range of conductivity is between 0.001 mS/cm and 850 mS/cm.

32. The device as claimed in claim 3, wherein a repetition frequency and/or a cycle frequency of the generation of the digital measurement signal is set up to the clock frequency of the alternating signal in a ratio of less than 1:100.

* * * * *